(12) United States Patent
Shimokawa et al.

(10) Patent No.: US 6,260,406 B1
(45) Date of Patent: Jul. 17, 2001

(54) DENSITOMETER USING MICROWAVES

(75) Inventors: Yoshiyuki Shimokawa, Fuchu; Masuo Suzuki, Koshigaya, both of (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/410,020

(22) Filed: Oct. 1, 1999

(30) Foreign Application Priority Data

Oct. 2, 1998 (JP) .................................................. 10-281412

(51) Int. Cl.$^7$ ........................................................ G01N 9/00
(52) U.S. Cl. ............................................................. 73/32 R
(58) Field of Search .............................. 73/32 R, 32 A, 73/602; 324/637, 639

(56) References Cited

U.S. PATENT DOCUMENTS

| | | | |
|---|---|---|---|
| 5,502,393 | * | 3/1996 | Yamaguchi et al. ................ 324/639 |
| 5,581,191 | * | 12/1996 | Yamaguchi ........................... 324/637 |
| 5,767,409 | * | 6/1998 | Yamaguchi ............................. 73/602 |

FOREIGN PATENT DOCUMENTS

| | | |
|---|---|---|
| 2-238348 | 9/1990 | (JP) . |
| 8-82606 | 3/1996 | (JP) . |
| 9-43181 | 2/1997 | (JP) . |

* cited by examiner

Primary Examiner—Richard A. Moller
(74) Attorney, Agent, or Firm—Finnegan, Henderson, Farabow, Garrett & Dunner, L.L.P.

(57) ABSTRACT

A densitometer using microwaves, which measures the density value of a to-be-measured substance in a to-be-measured liquid on the basis of a reception signal obtained by transmitting/receiving a microwave in/from the to-be-measured liquid by applicators, includes a clock source for generating a reference signal as a phase reference, an oscillator formed from a PLL circuit for generating a microwave having a frequency $f$ in synchronism with the reference signal from the clock source, an oscillator formed from a PLL circuit for generating a microwave having a frequency $f+\Delta f$ in synchronism with the reference signal from the clock source, a mixer for mixing the microwave from the oscillator, i.e., a reception signal having the frequency $f$ measured through the to-be-measured liquid with the microwave having the frequency $f+\Delta f$ from the oscillator, and a phase difference measuring section for comparing the phase of the output mixed by the mixer with that of the reference signal from the clock source to measure the phase difference.

9 Claims, 11 Drawing Sheets

DENSITOMETER USING MICROWAVES

BACKGROUND OF THE INVENTION

The present invention relates to a densitometer for measuring the density value of a to-be-measured substance such as a solid or suspension matter in a to-be-measured liquid using microwaves.

A densitometer using microwaves measures density by measuring the phase delay of microwaves on the basis of the fact that the microwaves have a phase delay almost proportional to the density value of a to-be-measured substance in a to-be-measured liquid as a medium.

Figures 1A, 1B:
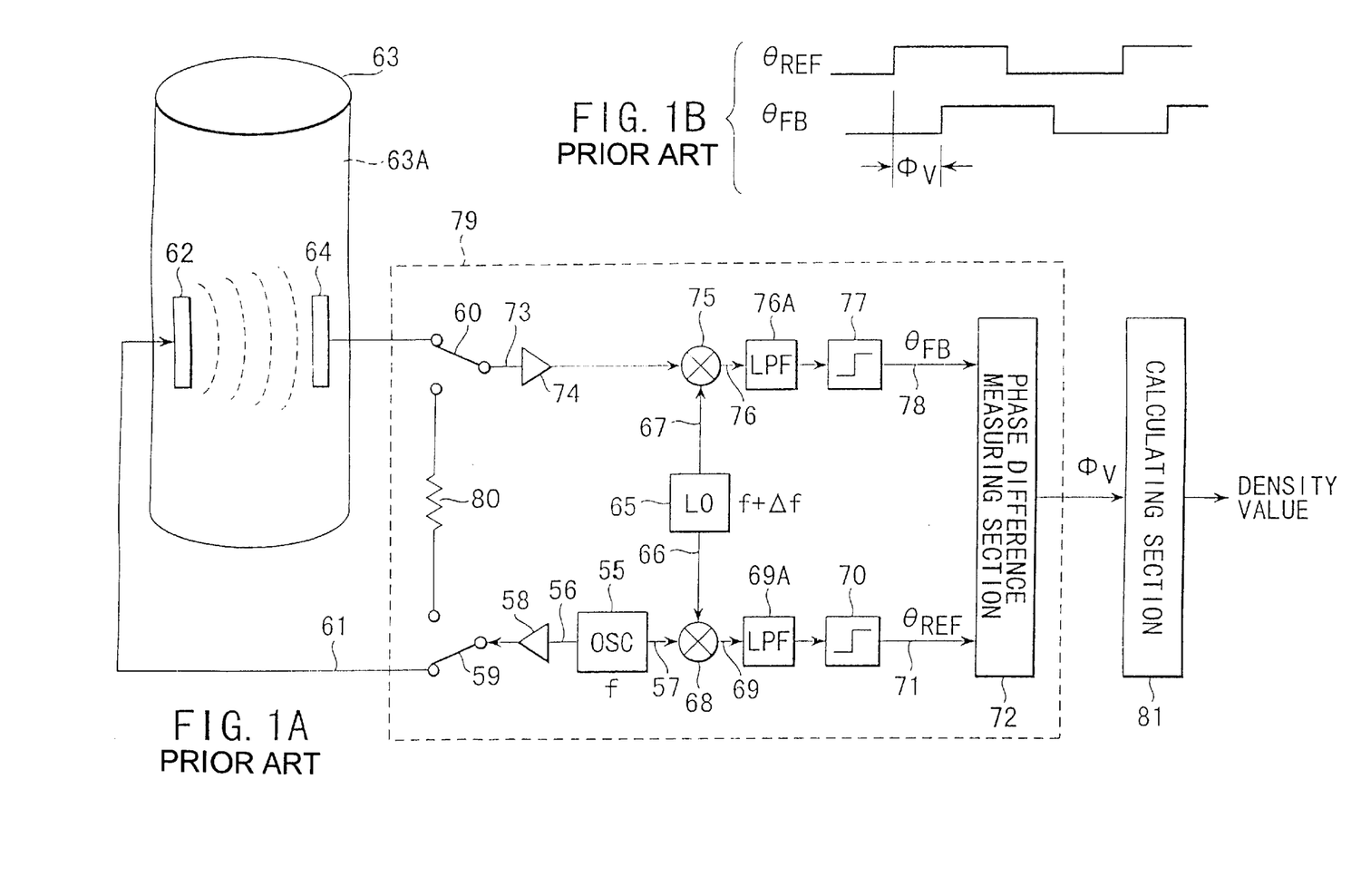
FIGS. 1A and 1B are a block diagram and a timing chart, respectively, showing a conventional densitometer using microwaves.

A densitometer of this type using microwaves comprises transmission and reception applicators 62 and 64 arranged in a tube 63 as microwave antennas, a microwave circuit 79 as an electronic circuit, and a calculating section 81, as shown in FIG. 1A. An oscillator 55 generates microwave signals 56 and 57 having a frequency $f$. The microwave signal 56 is amplified by an amplifier 58. When switches 59 and 60 are in the states shown in FIG. 1A, a transmission signal 61 is sent to the transmission applicator 62 in the tube 63 and then into the tube 63 in which a liquid 63A to be measured is passed. The signal is received by the reception applicator 64 which is set in the tube 63 to oppose the transmission applicator 62.

A reference oscillator 65 generates reference signals 66 and 67 having a frequency $f+\Delta f$ slightly different from the frequency $f$ of the microwave signals 56 and 57 from the oscillator 55. The microwave signal 57 and reference signal 66 are mixed by a mixer 68 to obtain a reference-side heterodyne output 69 as a difference frequency $\Delta f$. The output 69 is converted into a reference-side digital signal θREF 71 through a low-pass filter 69A and a comparator 70 whose threshold value is 0V, and sent to a phase difference measuring section 72.

A reception signal 73 received by the reception applicator 64 is amplified by an amplifier 74. The amplified reception signal 73 and the reference signal 67 are mixed by a mixer 75 to obtain a measurement-side heterodyne output 76 as a difference frequency $\Delta f$. The output 76 is supplied to a comparator 77 via a low-pass filter 76A, converted into a measurement-side digital signal θFB 78, and sent to the phase difference measuring section 72.

The phase difference measuring section 72 obtains a phase difference ΦV between the two digital outputs θREF 71 and θFB 78. As shown in FIG. 1B, the difference between the leading edges of the signals θREF and θFB is obtained as the phase difference ΦV.

In the microwave circuit 79 indicated by the dotted line, the phase changes due to, e.g., a change in temperature in the circuit to generate an error. To compensate for the error, the switches 59 and 60 are connected to the sides opposite to those in FIG. 1A to measure a phase difference ΦR through a fixed reference 80, and the phase difference ΦR is subtracted from the phase difference ΦV.

The fixed reference 80 uses an attenuator to drop the signal level of the microwave to the same level as that of the signal received by the applicator 64.

A phase difference Φ is given by Φ=ΦV−ΦR.

When data (calibration curve data) associated with the reference density is obtained in advance, a calculating section 81 can calculate, on the basis of the data, the density value of the to-be-measured substance in the to-be-measured liquid 63A from the obtained phase difference Φ.

Let D be the density value. The relationship between the density value D and the phase difference is essentially described by linear equation (1). Values a and b can be determined by measuring phase differences while changing the density value and performing regression analysis.

$$D = a\Phi + b \quad \ldots \quad (1)$$

In water as a conductive fluid to be measured, the following relationship holds between the attenuation and phase delay of a microwave, and a conductivity a, permittivity, and temperature t of the fluid to be measured:

$$\alpha = \frac{z_0}{\sqrt{2}} \frac{\sigma + \omega\varepsilon_0\varepsilon_r''}{\sqrt{1 + \sqrt{1 + \left(\frac{\sigma}{\omega\varepsilon_r'\varepsilon_0} + \frac{\varepsilon_r''}{\varepsilon_r'}\right)^2}}} \quad (2)$$

$$\beta = \frac{\omega\sqrt{\mu_r\varepsilon_r'}}{c_0\sqrt{2}} \sqrt{1 + \sqrt{1 + \left(\frac{\sigma}{\omega\varepsilon_r'\varepsilon_0} + \frac{\varepsilon_r''}{\varepsilon_r'}\right)^2}} \quad (3)$$

where σ is the conductivity of the fluid to be measured, and εr' and εr" are respectively the real part and imaginary part of the complex relative permittivity of the fluid to be measured.

As is well known, when the density of sludge or pulp as a substance to be measured changes, the effective permittivity changes accordingly. Especially, the permittivity real portion and the density value have high correlation.

When $$\frac{\sigma}{\omega\varepsilon_r'\varepsilon_0} + \frac{\varepsilon_r''}{\varepsilon_r'} \ll 1$$

in equations (2) and (3), the permittivity imaginary portion is small. When the conductivity is also low, we obtain $$\alpha = \frac{z_0}{\sqrt{2}}(\sigma + \omega\varepsilon_0\varepsilon_r'') \quad (4)$$

$$\beta = \frac{\omega\sqrt{\mu_r\varepsilon_r'}}{c_0\sqrt{2}} \quad (5)$$

The attenuation amount and phase delay are obtained from α and β obtained on the basis of equations (4) and (5). Let P0 be the transmission power, and P be the microwave power traveling in the z direction. Then, $$P = P0 \exp(-2\alpha z) \quad (6)$$

The attenuation amount is 20 αz/ln10 dB.

The phase delay is βz rad.

In the above-described scheme, the density value is obtained by obtaining the phase delay. As shown in equation (5), εr' is in proportion to β in the small change range of εr'. For this reason, the density value is obtained from βz. Since α has lower correlation than β, α is not directly used for density measurement.

The above-described conventional densitometer using microwaves has the following problems.

(a) When the temperature or conductivity of the liquid to be measured changes, the amount of attenuation of a microwave due to the liquid to be measured greatly changes. When the microwave attenuates to decrease the amplitude of the measurement-side heterodyne output 76, the switching time for phase difference measurement changes due to the influence of noise or drift in digitizing the reception signal with the comparator 77, resulting in a measurement error.

(b) Due to the same reason as in (a), when power of the reception signal 73 changes, the phase changes due to the non-linearity of the electronic circuit, resulting in a measurement error.

(c) The influence of temperature drift in the electronic circuit is compensated for by the fixed reference attenuator. When the signal level of the measurement-side heterodyne output 76 changes, the influence of temperature changes and therefore cannot be completely compensated for.

(d) The density value is obtained on the basis of a change in phase. For this reason, when the phase of the reception signal 73 exceeds 360°, the density value cannot be accurately obtained.

More specifically, when the tube diameter is large, or the substance to be measured has a high density, the phase changes by 360° or more, and the density value cannot be uniquely determined from the change in phase. In continuous measurement, the number of cycles can be estimated from previous/next measurements, as disclosed in, e.g., Jpn. Pat. Appln. KOKAI Publication No. 8-82606. However, when the tube empties and is filled with the liquid to be measured again, no accurate density value can be measured.

(e) The microwave is received through portions other than the liquid to be measured because of runaround or induction from the wiring pattern of the circuit, resulting in a measurement error.

(f) When bubbles are present in the liquid to be measured, the microwave traveling path becomes long, or the microwave is reflected and received through a plurality of paths, resulting in a measurement error.

(g) When the temperature or conductivity of the liquid to be measured changes, the phase of the microwave changes to generate an error. To prevent this, the temperature or conductivity need be measured and corrected. A method of measuring conductivity has been proposed, as disclosed in Jpn. Pat. Appln. KOKAI Publication No. 9-43181. However, a conductivity sensor is readily contaminated. This decreases the measurement accuracy or poses a problem of maintenance. Hence, this method can hardly be put into practical use.

(h) The microwave circuit is expensive and increases the cost of the device itself.

BRIEF SUMMARY OF THE INVENTION

It is an object of the present invention to provide a densitometer using microwaves, which can solve at least one of the above-described problems and accurately obtain the density value of a to-be-measured substance in a liquid to be measured.

The above object is achieved by a densitometer using microwaves, comprising
applicators set in a tube for flowing a to-be-measured liquid containing a to-be-measured substance, the applicators transmitting/receiving a microwave in/from the to-be-measured liquid,
a microwave circuit section for generating a microwave having a predetermined frequency and to be transmitted/received by the applicators and measuring a phase difference between the microwave that has passed through the to-be-measured liquid and a microwave that has not passed through the to-be-measured liquid, and
a calculating section for calculating a density value of the to-be-measured substance in the to-be-measured liquid on the basis of the phase difference from the microwave circuit section,
the microwave circuit section comprising
measurement microwave generating means for generating a measurement microwave to be transmitted to a to-be-measured fluid flowing through a measurement tube,
reference microwave generating means for generating a reference microwave having a frequency different from that of the measurement microwave,
microwave mixing means for mixing a reception signal obtained by receiving the measurement microwave transmitted to the to-be-measured fluid with the reference microwave,
phase reference signal generating means for generating a phase reference signal, and
phase difference measuring means for comparing a phase of an output from the microwave mixing means with that of the phase reference signal from the phase reference signal generating means to measure a phase difference.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

First Embodiment

Figure 2:
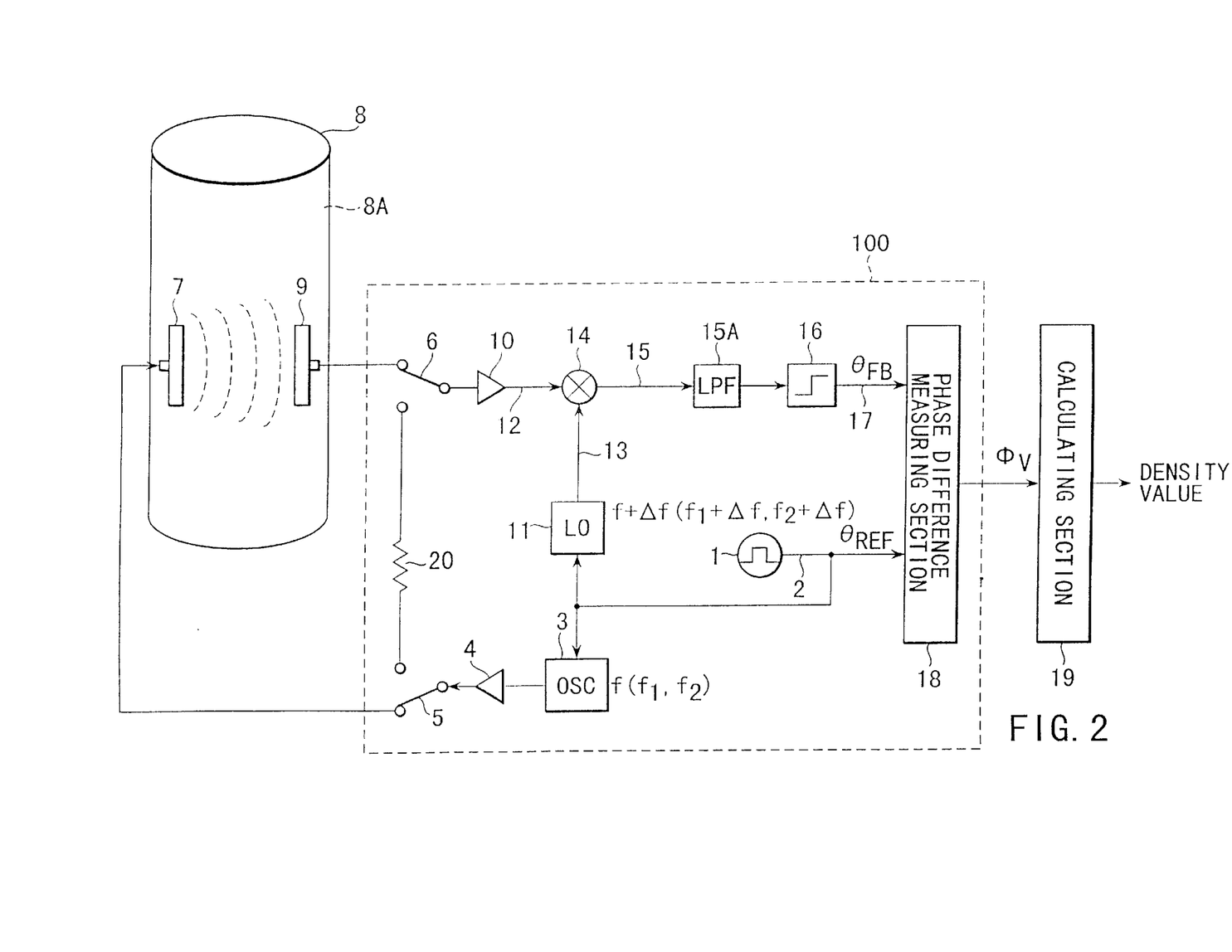
FIG. 2 is a block diagram showing a densitometer using microwaves according to the first embodiment of the present invention.

FIG. 2 is a block diagram showing a densitometer using microwaves according to the first embodiment. Referring to FIG. 2, a microwave circuit 100 has a clock source 1. The clock source 1 generates a reference signal θ REF 2 as a phase reference signal having a frequency lower than the microwave band. An oscillator 3 for generating a measurement microwave includes a PLL circuit (Phase-Locked Loop circuit). The oscillator 3 generates microwaves having different frequencies f1 and f2 in synchronism with the reference signal from the clock source 1 by using the low-frequency reference signal from the clock source 1 as a sync signal for the PLL circuit.

One of the microwaves from the oscillator 3 is amplified by an amplifier 4. When switches 5 and 6 are in the states shown in FIG. 2, the microwave is transmitted from a transmission applicator 7 to a liquid to be measured in a tube 8, received by a reception applicator 9, and amplified by an amplifier 10 to obtain a reception signal 12. An oscillator 11 for generating a reference microwave includes a PLL circuit, like the oscillator 3. The oscillator 11 generates, as reference signals 13, microwaves having frequencies f1+Δf and f2+Δf which are different from the frequencies f1 and f2 from the oscillator 3 by Δf and synchronous with the reference signal from the clock source 1 by using the low-frequency reference signal from the clock source 1 as a sync signal for the PLL circuit. A mixer 14 mixes the reception signal 12 with the reference signal 13 to obtain a heterodyne output 15 having the frequency Δf.

This heterodyne output 15 is passed through a low-pass filter 15A to attenuate unwanted high-frequency components and amplify the frequency Δf component. A comparator 16 receives the heterodyne output 15 and outputs a measurement digital signal θFB 17. A phase difference measuring section 18 compares the measurement digital signal 17 with the reference signal 2 from the clock source 1 and outputs a phase difference Φ. A calculating section 19 calculates the density value of the to-be-measured liquid on the basis of the phase difference Φ from the phase difference measuring section 18 and outputs the density value.

In the densitometer of the first embodiment having the above arrangement, the clock source 1 generates the reference signal 2 as a phase reference, two microwaves are generated in synchronism with the reference signal 2, the reception signal 12 measured using the microwave is mixed with the microwave 13, and the phase of the mixed signal is compared with that of the reference signal 2 from the clock source 1. With this arrangement, the number of mixers as microwave mixing means can be decreased to one, unlike the prior art shown in FIG. 1 wherein two mixers are required.

Since an expensive microwave element can be omitted, and the comparator after mixing can also be omitted, a simple and reliable circuit can be realized at low cost. This is because the two microwave oscillators 3 and 11 are controlled by the PLL circuits to completely synchronize with the clock source 1 with a frequency lower than the microwave band, and the frequency of the signal from the clock source 1 can be used as a reference frequency.

The reference signal θREF 2 used for phase difference measurement is used to obtain a relative value to the measurement digital signal θFB 17. The absolute value of the reference signal θREF 2 is obtained from the relative value between the reference signal θREF 2 and measurement digital signal θFB 17, which is obtained from a fixed reference 20. The absolute value is compared with calibration curve data prepared in advance, thereby calculating the density value of the to-be-measured substance in the liquid to be measured.

As described above, in the densitometer of the first embodiment, the low-frequency reference signal 2 is generated by the clock source 1 as a phase reference. In synchronism with the low-frequency reference signal 2, two microwaves are generated under the PLL control. One microwave is passed through the to-be-measured liquid to obtain the reception signal. The reception signal is mixed with the other microwave. The phase of the mixed signal is compared with that of the reference signal 2 from the clock source 1. With this arrangement, a simple and reliable circuit can be realized at low cost.

First Modification of First Embodiment

Figure 3:
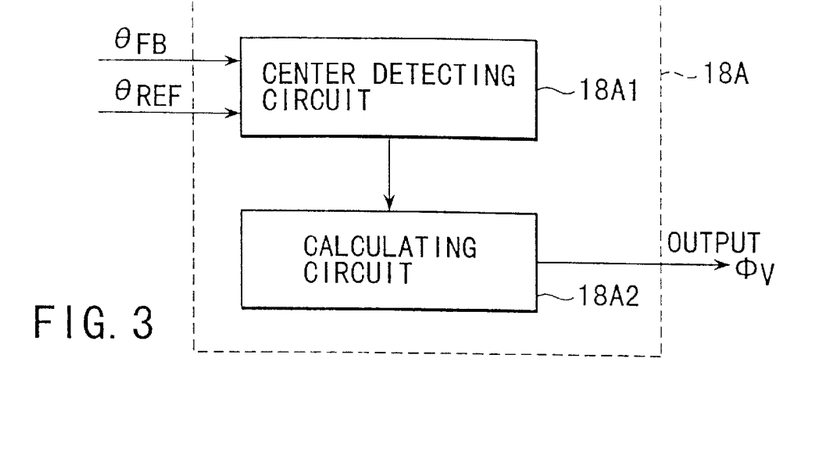
FIG. 3 is a block diagram showing the main part of a phase difference measuring section in a modification of the densitometer according to the first embodiment.

The densitometer of this modification has, as a phase difference measuring section 18', a center phase calculating section 18A for calculating a phase difference at the substantial center position of the phase difference, as shown in FIG. 3. The center phase calculating section 18A comprises a center detecting circuit 18A1 and calculating circuit 18A2.

Figure 4A:
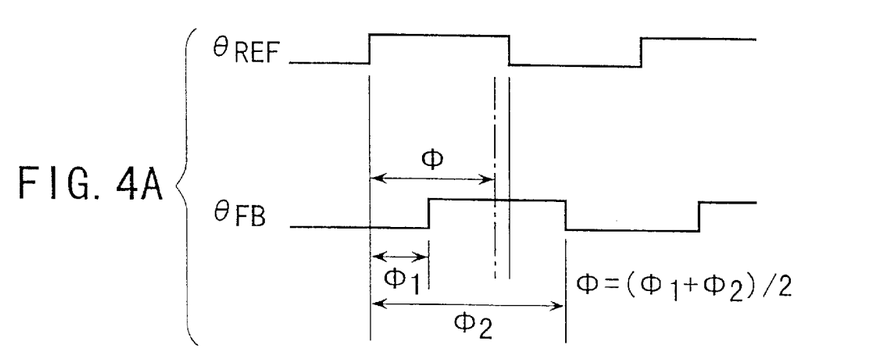
FIGS. 4A to 4C are timing charts for explaining the principle of phase difference measurement in the modification.

FIGS. 4A to 4C are timing charts for explaining the operation of the center phase calculating section 18A shown in FIG. 3, in which θREF represents the reference signal 2 and θFB represents the measurement digital signal 17. In the above-described conventional scheme, a difference θ1 between the signal leading edges is obtained. In the modification shown in FIG. 4A, the average value of the differences Φ1 and Φ2 is obtained. More specifically, the center detecting circuit 18A1 detects the difference Φ1 between the leading edge of the reference signal θREF and the leading edge of the measurement digital signal θFB and the difference Φ2 between the leading edge of the reference signal θREF and the trailing edge of the measurement digital signal θFB. The calculating circuit 18A2 calculates the average value Φ=(Φ1+Φ2)/2 from the differences Φ1 and Φ2 detected by the center detecting circuit 18A1.

Figure 4B:
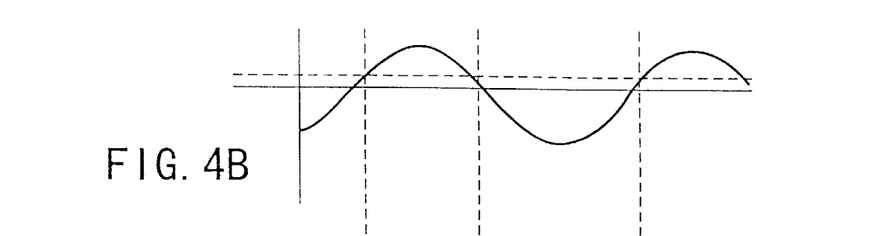
Figure 4C:
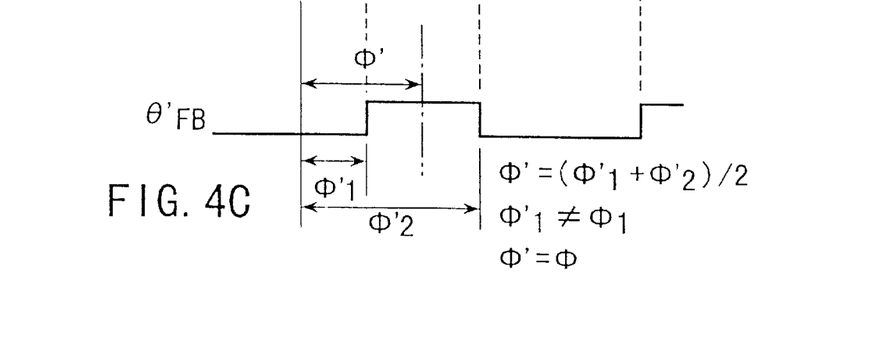

The center detecting circuit 18A1 has the following advantage. As shown in FIGS. 4B and 4C, when the ratio between "0" and "1" of the measurement digital signal θFB varies because of the DC component of the heterodyne output 15, drift, or the threshold value of the comparator 16 being not strictly 0V, an error occurs in the above-described conventional scheme. However, when the center scheme of this modification is employed, the density value can be accurately measured without any errors. This scheme is particularly effective when the microwave greatly attenuates and the amplitude of the heterodyne output 15 becomes small.

As described above, the densitometer of this modification measures the phase difference at the center position. This makes it possible to accurately measure the density value without any measurement errors.

This example has been explained as a modification of the first embodiment. However, this example is not limited to this and can also be applied to the phase difference measuring section of the above-described prior art shown in FIG. 1A.

Second Modification of First Embodiment

In this modification, as shown in FIG. 2, the oscillator 3 generates microwaves with the frequencies f1 and f2, and the reference oscillator 11 generates microwaves with the frequencies f1+Δf and f2+Δf. The phase difference measuring section 18 measures the phase difference on the basis of the plurality of microwaves having the same frequency difference. A phase difference of 360° or more is measured by switching these microwaves.

In this modification, a plurality of microwaves having the same frequency difference are generated and switched to measure a phase difference of 360° or more. Even when the phase changes beyond 360°, an accurate phase change amount can be obtained. More specifically, in this modification, the two sets of frequencies f1 and f2, and f1+Δf and f2+Δf are generated, and a phase difference for each combination is measured. The number of cycles of the phase change is obtained from the two phase differences, and a phase change exceeding 360° is obtained.

Let $\Phi 1$ and $\Phi 2$ be the two phase differences. Let $\Phi 10$ and $\Phi 20$ be the phase differences for the frequencies f1 and f2 when the density value is zero. Assume that the frequencies f1 and f2 change as follows in accordance with a change in density value.

$$f1: \Phi 10 \to \Phi 1 + 2\pi m$$

(m is 0 or a positive integer)

$$f2: \Phi 20 \to \Phi 2 + 2\pi n$$

(n is 0 or a positive integer)
where m and n are the numbers of cycles.

Phase difference change amounts $\Delta\Phi 1$ and $\Delta\Phi 2$ are respectively given by $$\Delta\Phi 1 = \Phi 1 + 2\pi m - \Phi 10 \quad (7)$$

$$\Delta\Phi 2 = \Phi 2 + 2\pi n - \Phi 20 \quad (8)$$

Letting $\beta 1$ and $\beta 2$ be the phase change rates for the frequencies f1 and f2, we have $$\Delta\Phi 2 = (\beta 2/\beta 1) \cdot \Delta\Phi 1 \quad (9)$$

Subtracting the right-hand side of equation (9) from the left-hand side, and substituting equations (7) and (8) into equation (9) yield $$\Phi 2 + 2\pi n - \Phi 20 - (\beta 2/\beta 1) \cdot (\Phi 1 + 2\pi m - \Phi 10) = 0 \quad (10)$$

Actually, since the phase difference measurement value has an error, various values of integers m and u are substituted into the left-hand side of equation (10) to obtain a combination of values m and n with which the measurement value falls within the error allowable range.

On the basis of the values m and n, the phase difference change amounts $\Delta\Phi 1$ and $\Delta\Phi 2$ are obtained from equations (8) and (9), and the density value is calculated.

The phase change rates $\beta 1$ and $\beta 2$ equal the frequencies f1 and f2 if $\epsilon r'$ is the same. Since the frequencies f1 and f2 take relatively close values, $\epsilon r'$ does not largely change in general.

As described above, in the densitometer of this modification, a plurality of microwaves having the same frequency difference are generated by the oscillators 3 and 11 serving as microwave sources generate and switched to measure a phase difference of 360° or more. When the phase changes beyond 360°, an accurate phase change amount can be obtained without using the method in Jpn. Pat. Appln. KOKAI Publication No. 8-82606.

According to this modification, even when the density is high, or the tube temporarily empties and is filled with the to-be-measured liquid again, an accurate density value can be measured.

This example can also be applied to the shown in FIG. 1A.

Second Embodiment

Figure 5:
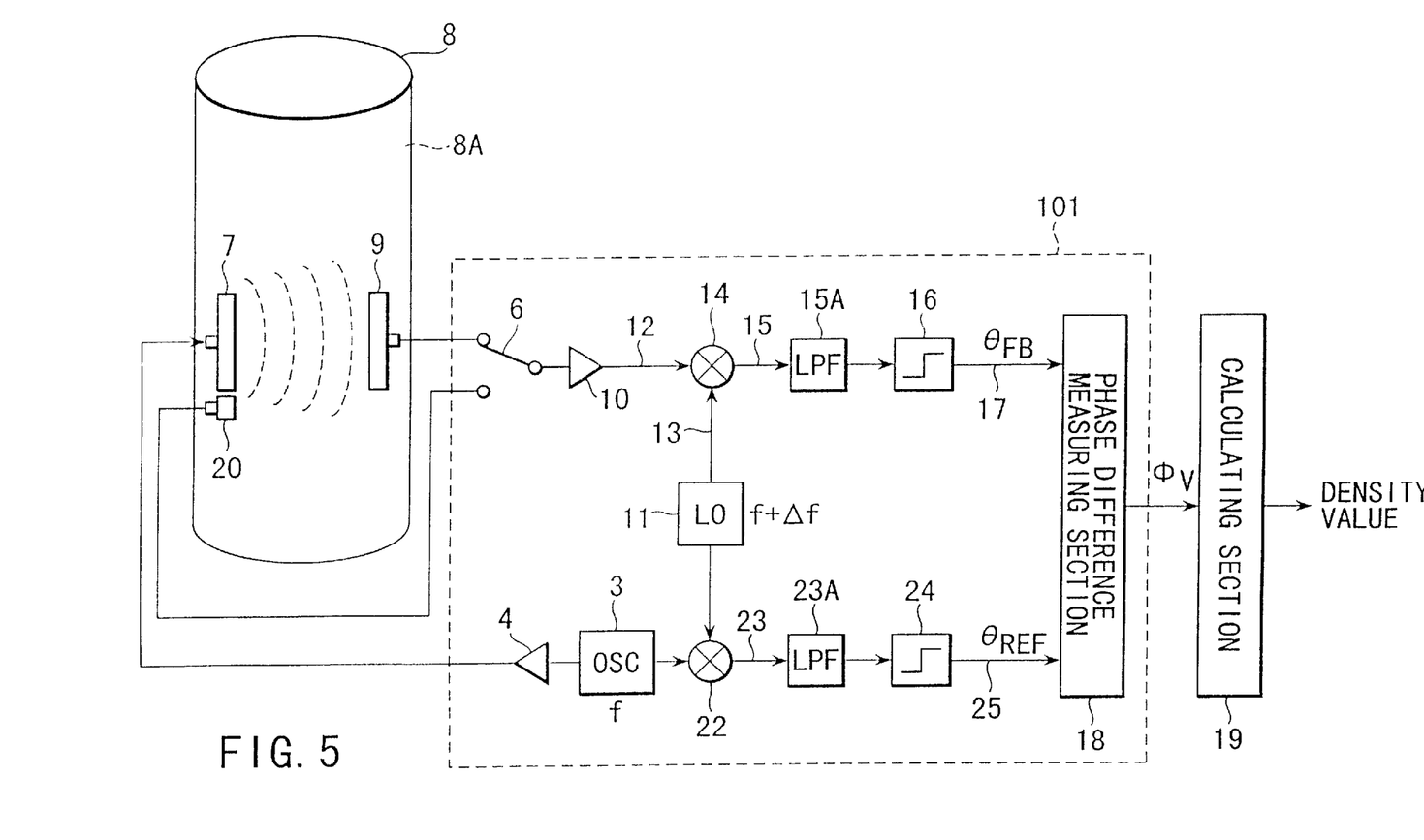
FIG. 5 is a block diagram showing a densitometer according to the second embodiment of the present invention.

FIG. 5 is a block diagram showing a densitometer according to the second embodiment. In the densitometer of the second embodiment, a reference terminal 26 is located adjacent to a transmission applicator 7. The reference terminal 26 functions as a reference applicator (antenna) for supplying compensation data in place of the fixed reference 20 using an attenuator in FIG. 2.

In the second embodiment, the distance from a reception applicator 9 to the input of a microwave circuit 101 as an electronic circuit can be made almost equal to that from the reference terminal 26 to the input of the microwave circuit 101. For this reason, fixed reference data obtained from the reference terminal 26 can compensate for the phase delay due to the cables to the transmission applicator 7 and reception applicator 9. By compensating for the phase delay, any phase variation due to temperature change can be removed, and accurate measurement can be performed.

In the above-described example, a fixed reference using an attenuator is used. When the temperature of the cable changes, an error may occur. More specifically, in the above-described prior art, since the phase changes due to a change in temperature in the circuit, a phase difference $\Phi R$ passing through the fixed reference is measured and subtracted from a phase difference $\Phi V$ to compensate for the phase change.

In the second embodiment, however, the reference terminal 26 functioning as a reference applicator (antenna) is placed adjacent to the transmission applicator 7, and a signal received by this reference terminal is used as a fixed reference. A switch 6 is connected to the reference terminal 26 side to measure the phase difference $\Phi R$ through the fixed reference. When the phase difference $\Phi R$ is subtracted from the phase difference $\Phi V$, the error can be compensated for.

In the second embodiment, as the reference terminal 26, an applicator for receiving a radio wave from the transmission applicator 7 is used. However, an applicator different from the transmission applicator 7 may be prepared to receive part of the power to be received by the transmission applicator 7.

As described above, in the densitometer of the second embodiment, a phase difference relative to fixed reference is measured and compensated for. Hence, even when the phase changes due to a change in temperature in the circuit, the density value can be accurately measured.

The second embodiment can also be applied to the prior art shown in FIG. 1A.

Third Embodiment

Figure 6:
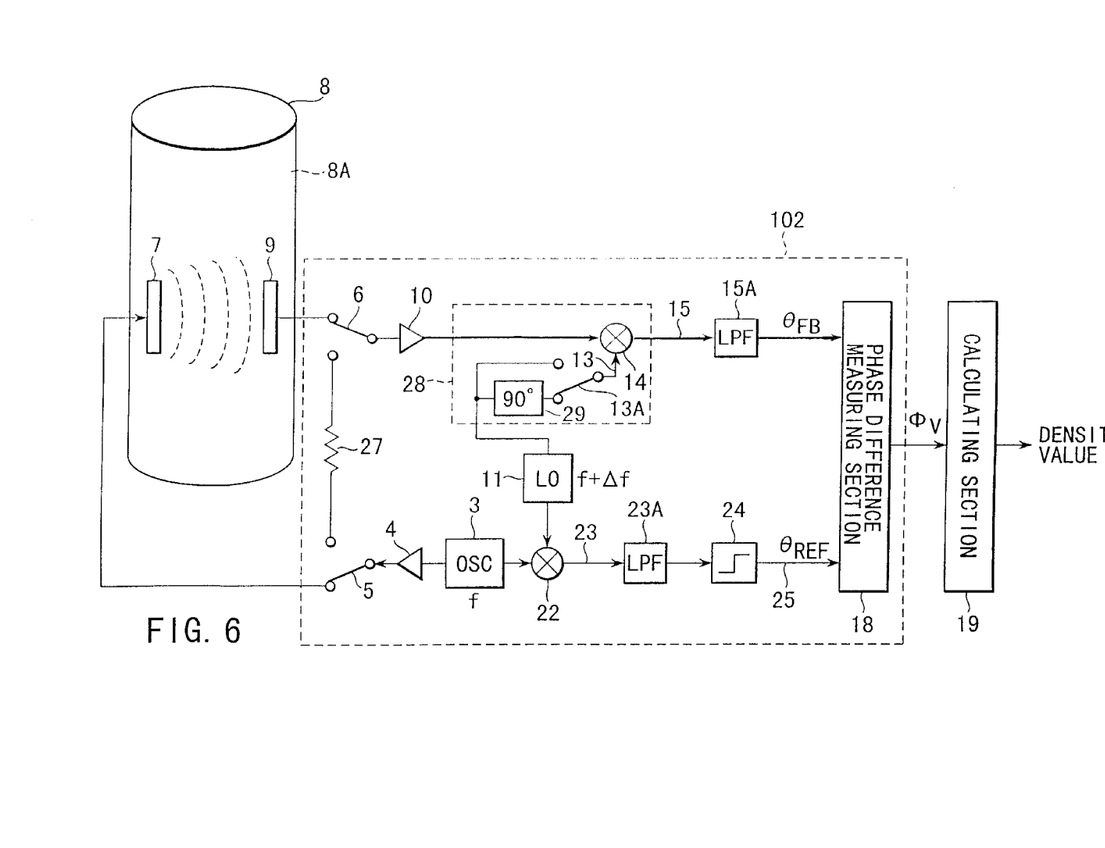
FIG. 6 is a block diagram showing a densitometer according to the third embodiment of the present invention.

FIG. 6 is a block diagram showing a densitometer according to the third embodiment. The same reference numerals as in FIG. 2 denote the same parts in FIG. 6, and a detailed description thereof will be omitted: only different portions will be described below. In the third embodiment, the mixer 14 portion in the above embodiments is replaced by a frequency mixing section 28. The frequency mixing section 28 provides reference signals 13 with a plurality of phases. In this embodiment, two microwaves 90° out of phase with each other are generated and mixed with the measurement signal by a mixer 14. The two microwaves 90° out of phase are generated by a hybrid 29. A fixed reference 27 uses an attenuator.

In the densitometer of the third embodiment, a heterodyne output 15 is obtained by measuring the phase difference using microwaves with a plurality of phase values. For this reason, even when runaround or induction from the wiring pattern of the circuit occurs, the density value can be accurately measured because the phase difference is measured using a plurality of phases and compensated for.

Since the hybrid 29 as a microwave element used in a portable telephone or the like is easily available, microwaves having a phase difference of 90° or an integer multiple of 90° can be easily generated.

Figure 7A:
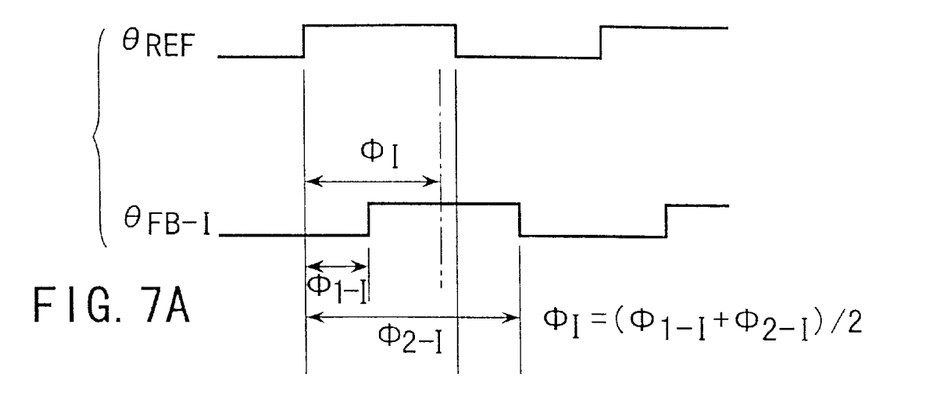
FIGS. 7A to 7C are views for explaining the principle of phase difference measurement using two microwaves with a phase difference of 90° in the densitometer of the third embodiment.
Figure 7B:
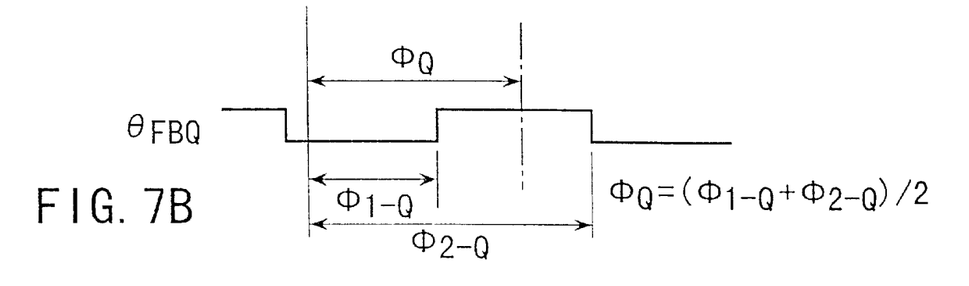

More specifically, in phase measurement of this embodiment, as shown in FIGS. 7A and 7B, heterodyne outputs θFB-I and θFB-Q which are 90° out of phase are obtained. A phase difference $\Phi I$ between the signal θFB-I and a reference signal θREF, and a phase difference $\Phi Q$ between the signal θFB-Q and the reference signal θREF are measured. A phase difference measuring section 18 calculates the average value $\Phi=(\Phi I+\Phi Q)/2$ as a phase difference for density value calculation.

Figure 7C:
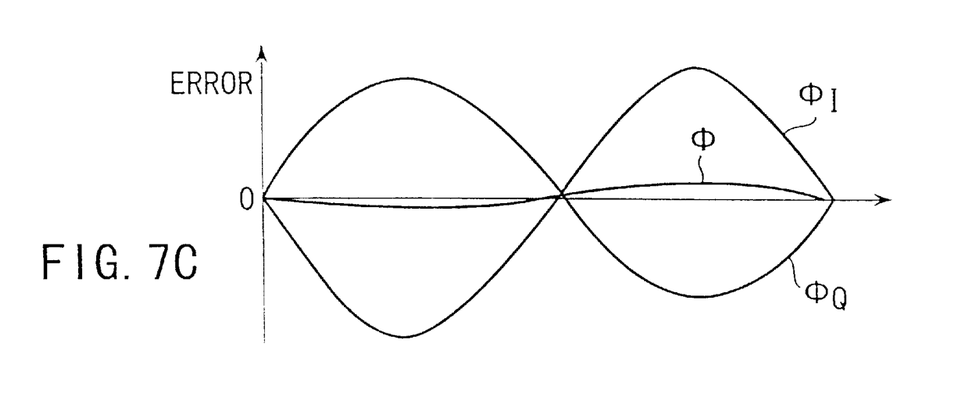

In this scheme, assume that the phase of the microwave which has passed through the liquid to be measured changes 360° from a certain reference. FIG. 7C shows typical characteristics of an error in the phase $\Phi$ measured by experiments. Because of the disturbance as a fixed phase due to runaround or induction from the wiring pattern of the circuit, the phase differences $\Phi I$ and $\Phi Q$ have nonlinear errors of sine components. However, the errors are canceled in the phase $\Phi$ obtained by averaging the phase differences $\Phi I$ and $\Phi Q$, so the phase $\Phi$ has good linearity.

In the third embodiment, two phases different by 90° are used. Alternatively, two phases different by 180° or four phases of 0°, 90°, 180°, and 270° may be used for measurement.

In the third embodiment, the phase of the reference signal is changed. A scheme of changing the phase of the reception signal may be used. Alternatively, two circuits may be prepared for 0° and 90°, respectively.

As described above, the densitometer of this embodiment measures density value by measuring the phase difference using a plurality of phases and compensating for the phase difference. Hence, even when runaround or induction from the wiring pattern of the circuit occurs, the density value can be accurately measured. This scheme is particularly effective when the power of the received microwave is small.

Since phases with a phase difference of 90° or an integer multiple of 90° are generated, the circuit can be easily realized using the hybrid 29.

Fourth Embodiment

Figure 8:
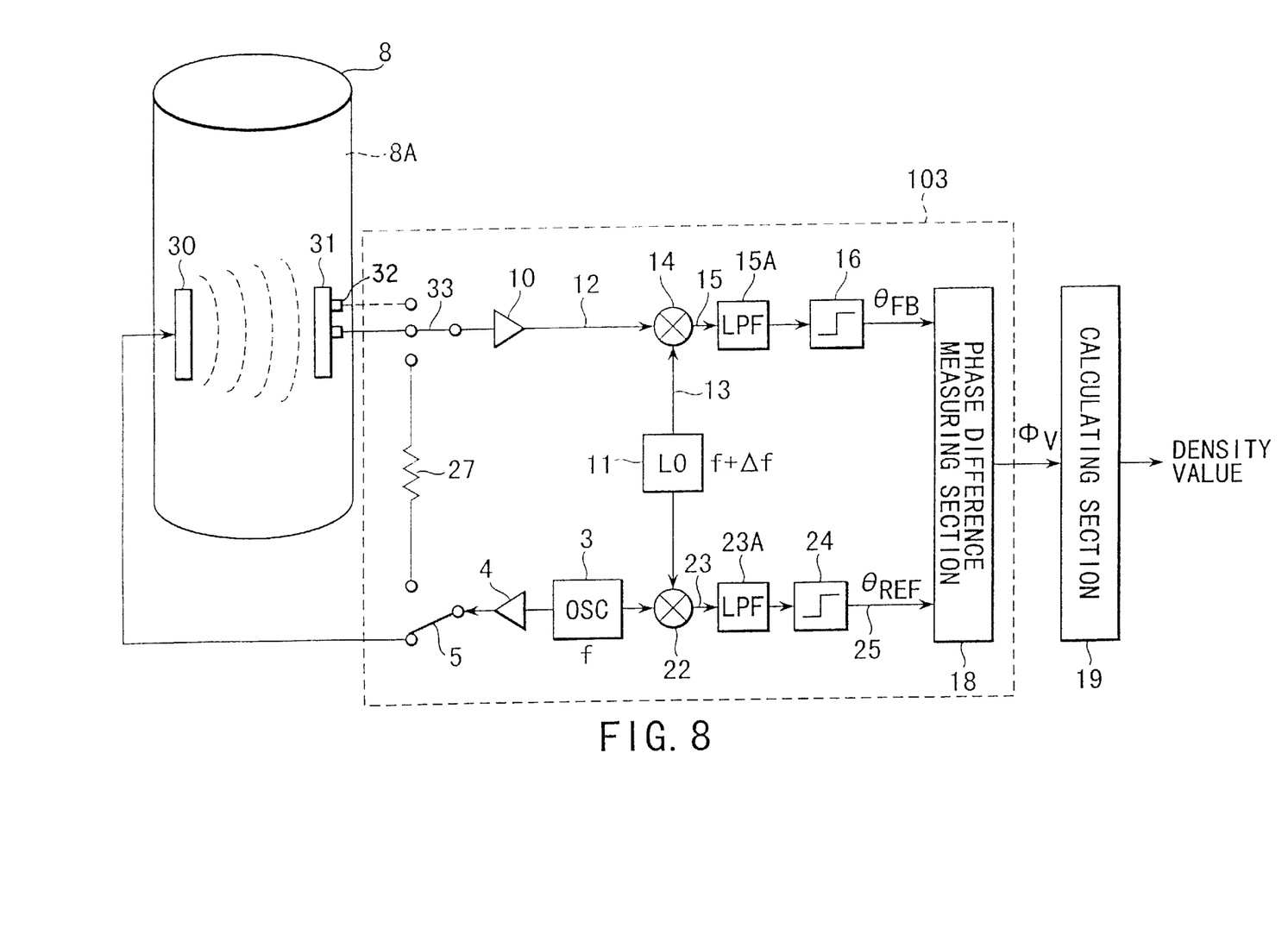
FIG. 8 is a block diagram showing a densitometer according to the fourth embodiment of the present invention.

FIG. 8 is a block diagram showing a densitometer according to the fourth embodiment. A transmission applicator 30 has a function of sending a linearly or circularly polarized microwave. A reception applicator 31 has a second terminal 32. A switch 33 in the state shown in FIG. 8 is connected to the second terminal 32 side. When a linearly polarized wave is transmitted, a microwave in phase with the transmitted microwave, and a microwave in phase quadrature with the in-phase microwave are received. When a circularly polarized wave is transmitted, a microwave in the same rotation direction as that of the transmitted microwave, and a microwave in the reverse direction of the transmitted microwave are received. A microwave circuit 103 has substantially the same arrangement as in FIG. 1.

When the medium is a liquid to be measured, and the liquid to be measured contains bubbles, the microwave is reflected by the bubbles to change the direction of the plane of polarization or the direction of rotation. The multiple-reflected microwave is received by the second terminal 32.

The amount of the multiple-reflected microwave has positive correlation with the amount of bubbles. A calculating section 19 calculates the amount of bubbles from the two signals and compensates for the phase measurement value.

In the densitometer of the fourth embodiment with the above arrangement, a linearly or circularly polarized microwave is sent. When a linearly polarized wave is transmitted, a microwave in phase with the transmitted microwave, and a microwave in phase quadrature with the in-phase microwave are received. When a circularly polarized wave is transmitted, microwaves in the same rotation direction as that of the transmitted microwave, and a microwave in the reverse direction of the transmitted microwave are detected. In addition, the amount of bubbles is calculated on the basis of the two signals to correct the phase measurement value. Even when the liquid to be measured has bubbles, the amount of bubbles is measured, and the influence of bubbles is compensated for. Hence, the density value can be accurately measured.

The reflection amount of a linearly or circularly polarized wave can be measured as the intensity of the microwave detected by the second terminal 32 of the reception applicator 31. When the amount of bubbles, the intensity of the microwave, and the characteristics of phase change are obtained in advance, the amount of bubbles can be measured to compensate for the influence of bubbles on the phase.

Figure 9A:
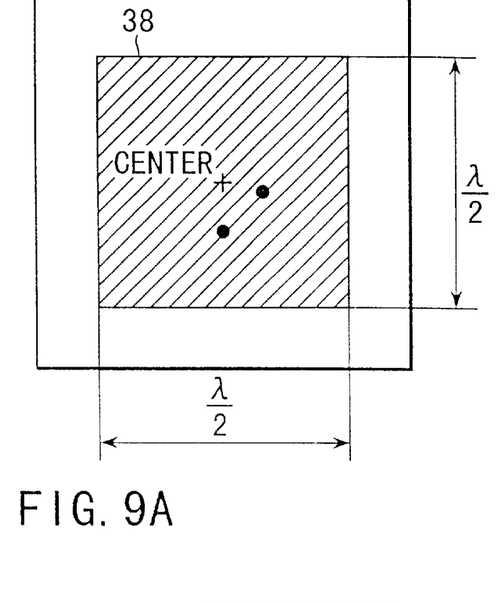
FIGS. 9A to 9D are views showing examples of the applicator of the densitometer according to the fourth embodiment.

A more detailed description will be made below. The transmission applicator 30 and reception applicator 31 have a common portion. FIG. 9A shows the basic arrangement of an applicator. Referring to FIG. 9A, a substrate 34 is formed from a dielectric material. A pattern 35 is a square solid pattern on the upper surface side and is formed from a thin metal film. The length of one side is $\lambda/2$ ($\lambda$ is the wavelength of a microwave to be used). The wavelength $\lambda$ is shortened to $1/\sqrt{\epsilon_\pi}$ compared to that in vacuum because the pattern is on the substrate 34. The pattern 35 also has terminals 36 and 37.

The terminal 36 is on the lower side of the center of the pattern 35 and is separated from the center by about ⅓ the distance between the center and each side. The terminal 37 is on the right side of the center of the pattern 35 and is separated from the center by about ⅓ the distance between the center and each side.

A pattern 38 is a solid ground pattern (thin metal film) on the lower surface side and has holes for passing the leads from the terminals 36 and 37.

The transmission applicator 30 and reception applicator 31 are set such that their terminals 36 and 37 accurately oppose each other (lines connecting the centers of the applicators and the terminals 36 are parallel).

Figure 9B:
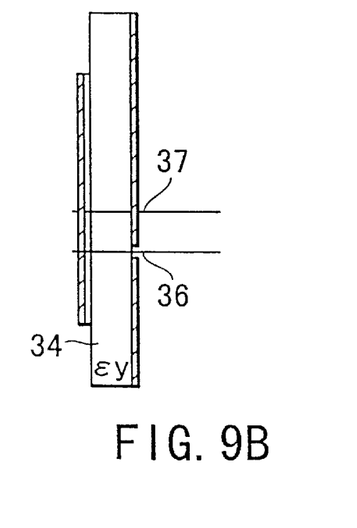

When a linearly polarized wave is to be sent from the transmission applicator 30, power need be fed to only the terminal 36 without setting the terminal 37. When a circularly polarized wave is to be sent from the transmission applicator 30, a hybrid 40 generates, from a transmitted microwave 39, a microwave 41 and a microwave 42 which is 90° out of phase, as shown in FIG. 9B. The microwave 41 is fed to the terminal 36, and the microwave 42 is fed to the terminal 37. The hybrid 40 has four terminals. The remaining terminal terminates into at a terminating resistor 43.

When a linearly polarized wave is used, the plane of polarization of the microwave reflected by an object in the to-be-measured liquid and received is different from that of the transmitted microwave. The reception applicator 31 receives a component having the same plane of polarization as that of the transmitted microwave at the terminal 36, and a component having a plane of polarization in phase quadrature with the transmitted microwave at the terminal 37. In this case, the terminal 37 corresponds to the second terminal 32.

Figure 9C:
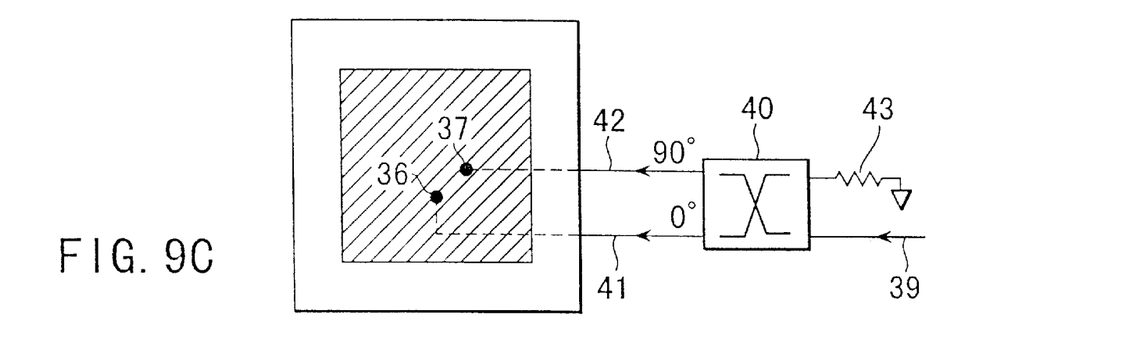
Figure 9D:
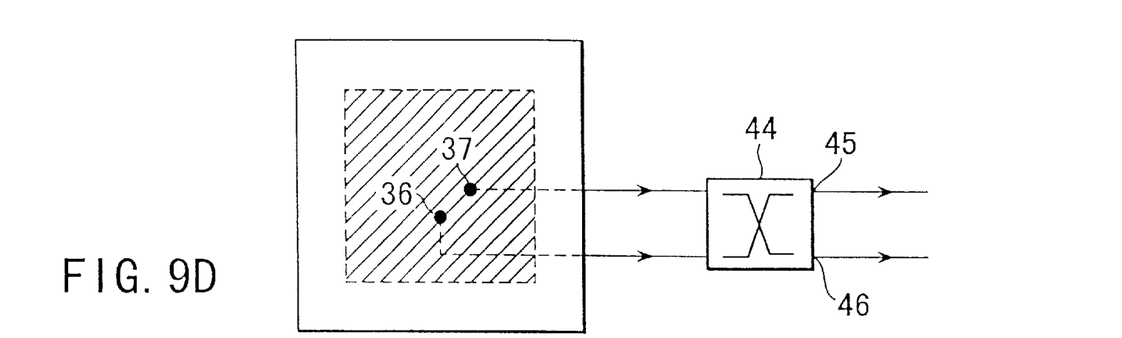

When a circularly polarized wave is used, the direction of rotation of the circularly polarized microwave reflected by an object in the to-be-measured liquid and received is reverse to that of the transmitted microwave. More specifically, as shown in FIG. 9C, the reception applicator 31 synthesizes, through a hybrid 44, the microwaves received at the terminals 36 and 37. Not to change the rotation direction, FIG. 9C is illustrated as a perspective view.

Assume that a microwave with a phase delay of 90° with respect to the microwave to the terminal 36 is fed to the terminal 37, as shown in FIG. 9B. When a wave in the same rotation direction as that of the transmitted microwave is received, the phase on the terminal 37 side delays by 90° from that on the terminal 36 side.

When a wave in the reverse rotation direction is received, the phase on the terminal 36 side delays by 90° from that on the terminal 37 side.

When a wave in the same rotation direction as that of the transmitted microwave is synthesized by the hybrid 44, the two microwaves add up because they are in phase. When a wave in the reverse rotation direction is synthesized, the two microwaves cancel each other because they have a phase difference of 180° Therefore, only a wave in the same rotation direction as that of the transmitted microwave is output from a terminal 45.

Conversely, a terminal 46 outputs only the wave in the reverse direction as the two microwaves add up. In this case, the terminal 46 corresponds to the second terminal 32.

As described above, in the fourth embodiment, the densitometer using microwaves measures the amount of bubbles and compensates for the influence of bubbles. Even when the liquid to be measured has bubbles, the density value can be accurately measured.

Fifth Embodiment

Figure 10:
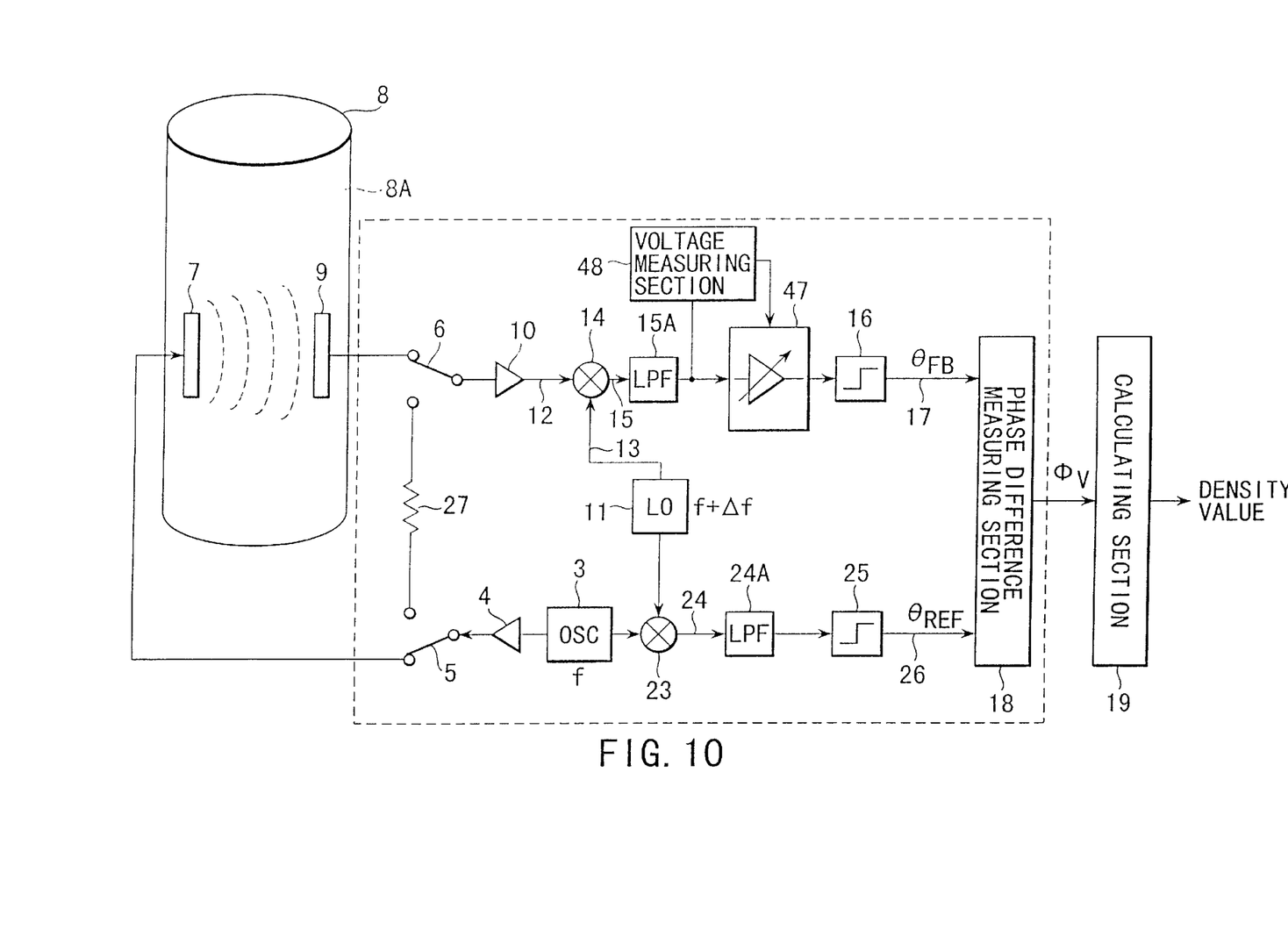
FIG. 10 is a block diagram showing a densitometer according to the fifth embodiment of the present invention.

FIG. 10 is a block diagram showing a densitometer using microwaves according to the fifth embodiment. The same reference numerals as in FIG. 4 denote the same parts in FIG. 10, and a detailed description thereof will be omitted: only different portions will be described below. In a microwave circuit 104 of the fifth embodiment, a heterodyne output 15 is controlled by a variable gain amplifier 47. The voltage of the heterodyne output 15 is measured by a voltage measuring section 48. On the basis of the measured value, the gain of the variable gain amplifier 47 is controlled to obtain a predetermined amplitude level for the heterodyne output 15 on the measurement side.

In the densitometer of the fifth embodiment, a predetermined amplitude is obtained for the output by the variable gain amplifier 47. Even when the microwave largely attenuates due to the temperature or conductivity of the liquid to be measured, the switching time of a comparator 16 does not change in accordance with a change in amplitude. Hence, no error is generated.

When the measurement signal level is low, the signal can be amplified to improve the S/N ratio. For this reason, the density value can be accurately measured.

As described above, in the densitometer of the fifth embodiment, the mixed signal is controlled to a predetermined level. Even when the microwave largely attenuates due to the temperature or conductivity of the liquid to be measured, no error occurs. When the measurement signal level is low, the signal can be amplified to improve the S/N ratio. Hence, the density value can be accurately measured.

Sixth Embodiment

Figure 11:
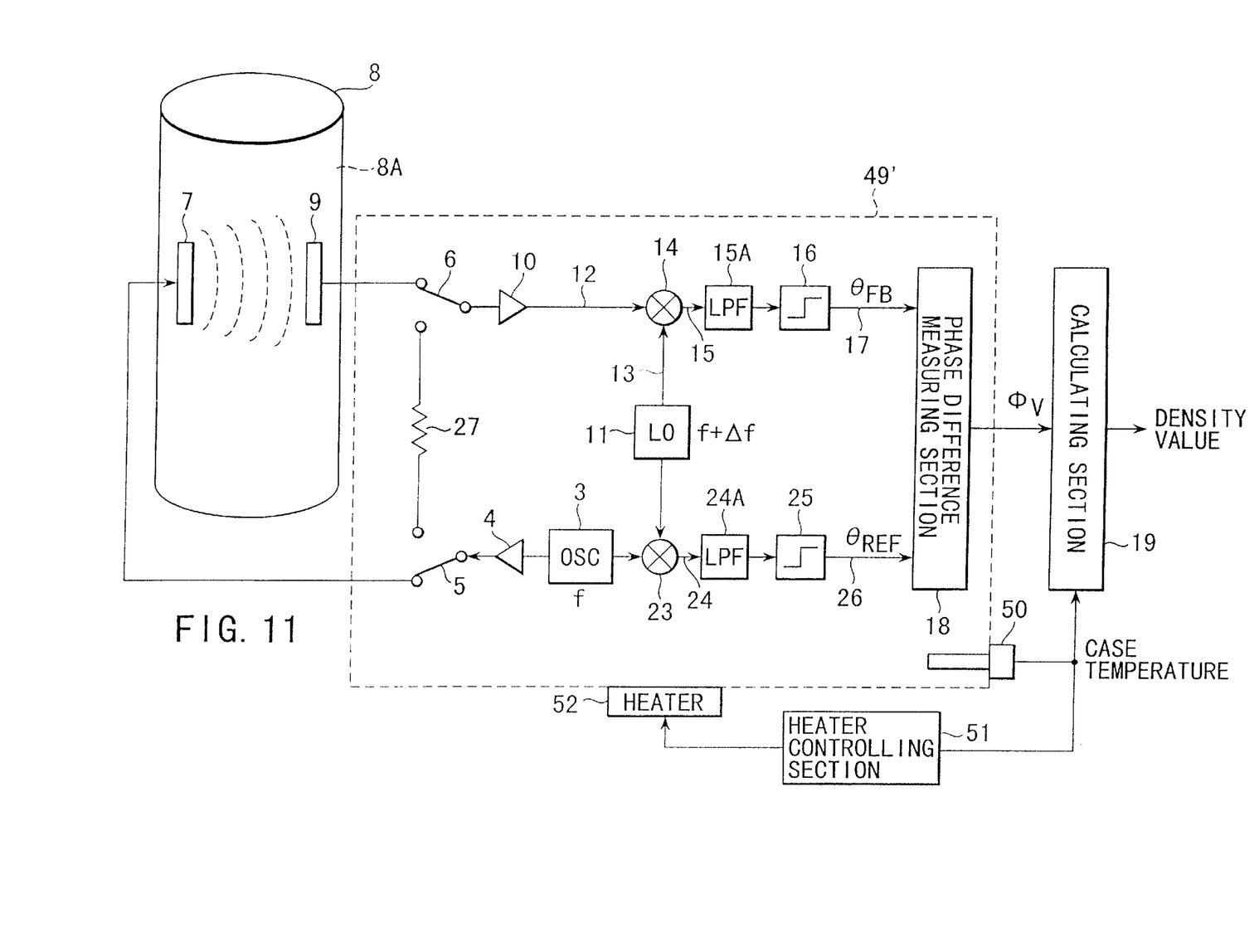
FIG. 11 is a block diagram showing a densitometer according to the sixth embodiment of the present invention.

FIG. 11 is a block diagram showing a densitometer using microwaves according to the sixth embodiment. The same reference numerals as in FIG. 4 denote the same parts in FIG. 11, and a detailed description thereof will be omitted: only different portions will be described below. A microwave circuit 49 is stored in a case 49'. A case thermometer 50 is set in the case 49'. The case thermometer 50 measures the case temperature. When the case temperature is equal to or smaller than a predetermined value, a heater controlling circuit 51 and heater 52 provided in the case 49' control the case temperature to a predetermined value.

When the circuit temperature is equal to or smaller than a predetermined value due to internal heat generation of the microwave circuit 49 or ambient temperature, a calculating section 19 corrects the measured value using a predetermined correction value.

In the densitometer of the sixth embodiment, the circuit temperature is controlled or corrected to a predetermined value. Even when the ambient temperature changes, a change in phase due to a change in circuit temperature can be prevented, and the density value can be accurately measured.

In addition, the low-temperature state upon power-on can be quickly changed to a stable state.

A circuit for cooling the device when the temperature increases becomes complex and is hard to control. Also, cooling components are expensive. However, since the calculating section 19 corrects the measured value, a simple circuit can be realized at low cost.

Seventh Embodiment

Figure 12:
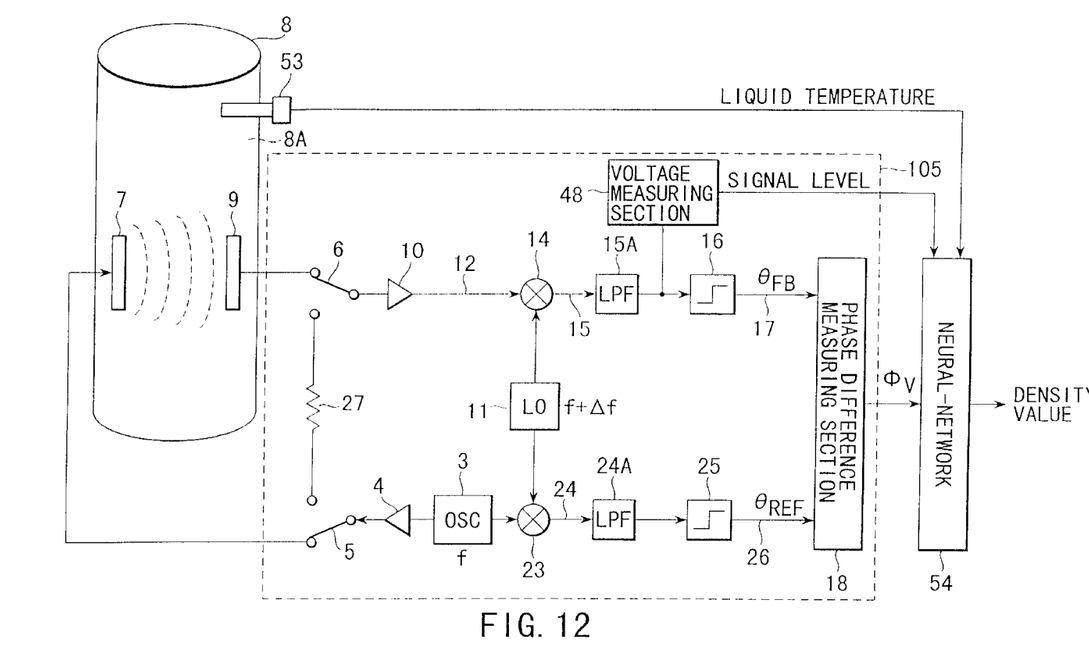
FIG. 12 is a block diagram showing a densitometer according to the seventh embodiment of the present invention.

FIG. 12 is a block diagram showing a densitometer using microwaves according to the seventh embodiment.

The same reference numerals as in FIG. 4 denote the same parts in FIG. 12, and a detailed description thereof will be omitted: only different portions will be described below. In a microwave circuit 105 of this embodiment, on the basis of the signal level measured by a voltage measuring section 48 and the temperature measured by a thermometer 53, the temperature of the liquid to be measured and a change in phase due to the signal level are corrected, thereby calculating the density value.

Additionally, the conductivity of the liquid to be measured and the phase correction value are calculated from the signal level and the temperature of the liquid to be measured, and a change in phase due to the conductivity is corrected, thereby calculating the density value.

Phase calculation including correction calculation have a large number of variables, and the relationships between phases and the variables are difficult to formulate. Hence, these calculations are implemented by a neural network 54 as a correction value calculation means. With the learning function of the neural network 54, the variables and actual density value and temperature are set by actual measurement and learned, thereby performing phase calculation and correction calculation.

In the densitometer of this embodiment, the conductivity of the liquid to be measured and the phase correction value are calculated on the basis of the level of the received signal and the temperature of the liquid to be measured. Even when the microwave largely attenuates due to the temperature or conductivity of the liquid to be measured, or the phase of the microwave changes in accordance with the temperature of the liquid to be measured, the density value can be accurately measured.

More specifically, when the conductivity of the liquid to be measured changes because of, e.g., salt mixing into the liquid, an attenuation rate a largely changes, as represented by equations (2) and (4).

When the temperature of the liquid to be measured changes, a relative permittivity ϵr changes. The temperature is measured and corrected using a predetermined value, thereby correcting the density value.

A phase difference $\Delta\theta$ is given by $$\Delta\theta=\{\theta 2-k(T-T0)-\gamma(E-E0)\}-\theta 1 \quad (11)$$

where

---

θ2: phase of liquid to be measured
θ1: phase of reference water in measurement
k: liquid temperature correction coefficient
T: liquid temperature
T0: temperature of reference water
γ: conductivity correction coefficient
E: attenuation amount by substance to be measured
E0: attenuation amount by reference water

---

A density value X is given by $$X=a\times\Delta\theta+b \quad (12)$$

where a is a constant of proportionality, and b is the bias.

As described above, when the conductivity changes, the attenuation rate α largely changes. A change in relative permittivity ϵr also influences the attenuation rate α. For this reason, γ in equation (11) is selected from a table prepared in accordance with a change in ϵr.

The phase difference $\Delta\theta$ is obtained on the basis of equation (11), and the density value is calculated from equation (12) using a and b obtained in advance.

When the correction value is calculated by the neural network 54, correction calculation can be easily realized.

As described above, in the seventh embodiment, the densitometer using microwaves corrects a change in phase due to changes in temperature and conductivity of the liquid to be measured and a change in signal level. Even when the microwave largely attenuates due to the temperature or conductivity of the liquid to be measured, or the phase of the microwave changes depending on the temperature of the liquid to be measured, the density value can be accurately measured.

Since the neural network 54 calculates the correction value, correction calculation can be easily realized.

In addition to the above-described embodiments, an appropriate combination of the plurality of embodiments can realize a higher-performance densitometer using microwaves.

As has been described above, according to the densitometer of the present invention, even when the temperature or conductivity of the liquid to be measured changes, the temperature in the device changes, runaround or induction of the microwave occurs, bubbles are generated, or a thick tube is used, the density value of a to-be-measured substance such as a solid or suspension matter in the to-be-measured liquid can be accurately measured.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A densitometer using microwaves, comprising an applicator section set in a tube for flowing a to-be-measured liquid containing a to-be-measured substance, said applicator section transmitting/receiving a microwave in/from the to-be-measured liquid, a microwave circuit section for generating a microwave having a predetermined frequency and to be transmitted/received by said applicator section and measuring a phase difference between the microwave that has passed through the to-be-measured liquid and a microwave that has not passed through the to-be-measured liquid, and a calculating section for calculating a density value of the to-be-measured substance in the to-be-measured liquid on the basis of the phase difference from said microwave circuit section, said microwave circuit section comprising measurement microwave generating means for generating a measurement microwave to be transmitted to a to-be-measured fluid flowing through a measurement tube, reference microwave generating means for generating a reference microwave having a frequency different from that of the measurement microwave, microwave mixing means for mixing a reception signal obtained by receiving the measurement microwave transmitted to the to-be-measured fluid with the reference microwave, phase reference signal generating means for generating a phase reference signal, and phase difference measuring means for comparing a phase of an output from said microwave mixing means with that of the phase reference signal from said phase reference signal generating means to measure a phase difference.

2. A densitometer according to claim 1, wherein said phase reference signal generating means supplies the phase reference signal to said measurement microwave generating means and said reference microwave generating means as a reference signal for microwave generation.

3. A densitometer according to claim 1, wherein each of said measurement microwave generating means and said reference microwave generating means comprises a phase-locked loop circuit for generating the microwave in synchronism with the phase reference signal from said phase reference signal generating means.

4. A densitometer according to claim 1, wherein said phase difference measuring means calculates a phase $\Phi 1$ between a leading edge of an output from said microwave mixing means and a leading edge of the phase reference signal from said phase reference signal generating means and a phase $\Phi 2$ between the leading edge of the output from said microwave mixing means and a trailing edge of the phase reference signal from said phase reference signal generating means, and $(\Phi 1+\Phi 2)/2$ is used as the phase difference.

5. A densitometer according to claim 1, wherein each of said measurement microwave generating means and said reference microwave generating means has means for generating a plurality of measurement or reference microwaves having different frequencies, and said phase difference measuring means measures phase differences in accordance with the measurement and reference microwaves having different frequencies, which are generated by said measurement microwave generating means and said reference microwave generating means, to measure a phase difference not less than 360°.

6. A densitometer according to claim 1, wherein said applicator section comprises a transmission applicator, a reception applicator, and a reference applicator near said transmission applicator, a transmission microwave transmitted from said transmission applicator is received by said reference applicator, and the received signal is used to compensate for an error in the phase difference.

7. A densitometer according to claim 1, wherein said reference microwave generating means comprises means for generating a plurality of reference microwaves having different phases, said microwave mixing means comprises means for mixing the reception signal obtained by receiving the measurement microwave transmitted to the to-be-measured fluid with each of the plurality of reference microwaves having different phases, and said phase difference measuring means comprises means for comparing a phase of each output from said plurality of microwave mixing means with the phase of the phase reference signal from said phase reference signal generating means to measure the phase difference.

8. A densitometer according to claim 1, wherein said reference microwave generating means includes a microwave element for generating a plurality of microwaves having phases different by a predetermined angle.

9. A densitometer according to claim 8, wherein said microwave element comprises a hybrid.

\* \* \* \* \*